US007014864B1

(12) United States Patent
Lipari et al.

(10) Patent No.: US 7,014,864 B1
(45) Date of Patent: *Mar. 21, 2006

(54) FORMULATIONS COMPRISING LIPID-REGULATING AGENTS

(75) Inventors: John M. Lipari, Racine, WI (US); Dawn M. Raymond, Solana Beach, CA (US); Tom Reiland, Gages Lake, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 656 days.

(21) Appl. No.: 09/216,242

(22) Filed: Dec. 18, 1998

(51) Int. Cl.
*A61K 31/19* (2006.01)
*A61K 9/48* (2006.01)
*A61K 31/215* (2006.01)

(52) U.S. Cl. .................... 424/451; 424/400; 424/455; 424/456; 514/506; 514/555; 514/576

(58) Field of Classification Search ............... 424/400, 424/450, 451, 455, 456; 514/506, 510, 555
See application file for complete search history.

(56) References Cited

U.S. PATENT DOCUMENTS

| 4,058,552 | A |   | 11/1977 | Mieville |
|---|---|---|---|---|
| 4,739,101 | A |   | 4/1988 | Bourgogne |
| 4,800,079 | A |   | 1/1989 | Boyer |
| 4,871,768 | A | * | 10/1989 | Bistrian |
| 4,895,726 | A |   | 1/1990 | Curtet |
| 4,925,676 | A |   | 5/1990 | Sellassie |
| 4,927,639 | A |   | 5/1990 | Sellassie |
| 4,957,746 | A |   | 9/1990 | Valducci |
| 4,961,890 | A |   | 10/1990 | Boyer |
| 5,030,447 | A |   | 7/1991 | Joshi |
| 5,180,589 | A |   | 1/1993 | Joshi |
| 5,494,936 | A | * | 2/1996 | Sanchez ..................... 514/712 |
| 5,506,230 | A | * | 4/1996 | Kikuchi |
| 5,545,628 | A |   | 8/1996 | Deboeck et al. |
| 5,645,856 | A | * | 7/1997 | Lacy ......................... 424/455 |
| 5,753,255 | A | * | 5/1998 | Chavkin |
| 5,827,536 | A |   | 10/1998 | Laruelle |
| 6,180,138 | B1 |   | 1/2001 | Engh et al. |

FOREIGN PATENT DOCUMENTS

| EP | 0793958 | 9/1997 |
|---|---|---|
| WO | WO 8201649 | 5/1982 |
| WO | WO 92/10996 | 4/1992 |
| WO | WO 95/24893 | 9/1995 |
| WO | WO 96/36318 | 11/1996 |

OTHER PUBLICATIONS

Ming-Thau Sheu et al., Characterization and Dissolution of Fenofibrate Solid Dispersion Systems; *International Journal of Pharmaceutics*, (1994), p. 137-146.

G. F. Palmieri et al., Characterization and Dissolution Studies of PEG 4000/Fenofibrate Solid Dispersions, *S.T.P. Pharma Sciences*, (1996), pp. 188-194.

* cited by examiner

*Primary Examiner*—Gollamudi S. Kishore
(74) *Attorney, Agent, or Firm*—Gregory W. Steele

(57) ABSTRACT

The present invention is directed to a formulation comprising a lipid-regulating agent dissolved in at least one structured lipid as the primary solvent medium for said agent. One or more emulsifiers may be added to the formulation.

8 Claims, 2 Drawing Sheets

FORMULATIONS COMPRISING LIPID-REGULATING AGENTS

FIELD OF THE INVENTION

The present invention relates to novel formulations for oral administration comprising lipid-regulating agents.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. No. 4,800,079 and U.S. Pat. No. 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granulate thus produced is dried.

PCT Publication No. WO 82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 describes the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

Gemfibrozil is another member of the fibrate class of lipid-regulating agents. U.S. Pat. No. 4,927,639 discloses a disintegratable formulation of gemfibrozil providing both immediate and sustained release, comprising a tablet compressed from a mixture of a first and second granulation, and a disintegration excipient operable to effect partial or complete disintegration in the stomach. The first granulation comprises finely divided particles of pure gemfibrozil granulated with at least one cellulose derivative, and the second granulation comprises finely divided particles of pure gemfibrozil granulated with a pharmaceutically-acceptable water soluble or insoluble polymer which are then uniformly coated with a pharmaceutically-acceptable (meth)acylate copolymer prior to admixture with the first granulation. The first and second granulations are present in the final composition in a ratio of from about 10:1 to about 1:10.

U.S. Pat. No. 4,925,676 discloses a disintegratable gemfibrozil tablet providing both immediate and enteric release, which is compressed from a mixture of a first granulation of gemfibrozil with at least one acid-disintegratable binder, and a second granulation formed from the first granulation, but regranulated or coated with an alkali-disintegratable formulation of at least one substantially alkali-soluble and substantially acid-insoluble polymer.

Another class of lipid-regulating agents are commonly known as statins, of which pravastatin and atorvastatin are members. U.S. Pat. Nos. 5,030,447 and 5,180,589 describe stable pharmaceutical compositions, which when dispersed in water have a pH of at least 9, and include a medicament which is sensitive to a low pH environment, such as pravastatin one or more fillers such as lactose and/or microcrystalline cellulose, one or more binders, such as microcrystalline cellulose (dry binder) or polyvinylpyrrolidone (wet binder), one or more disintegrating agents such as croscarmellose sodium, one or more lubricants such as magnesium stearate and one or more basifying agents such as magnesium oxide.

It is an object of the present invention to provide formulations for oral administration comprising lipid-regulating agents having enhanced bioavailability when compared to commercially available formulations.

SUMMARY OF THE INVENTION

The present invention is directed to formulations for oral administration comprising a lipid-regulating agent, further comprising at least one structured lipid as the primary solvent medium for the lipid-regulating agent. One or more emulsifiers may be added to the formulation.

The formulation may be administered directly, diluted into an appropriate vehicle for administration, encapsulated into soft or hard gelatin shells or capsules for administration, or administered by other means obvious to those skilled in the art.

DETAILED DESCRIPTION OF THE INVENTION

Figure 1:
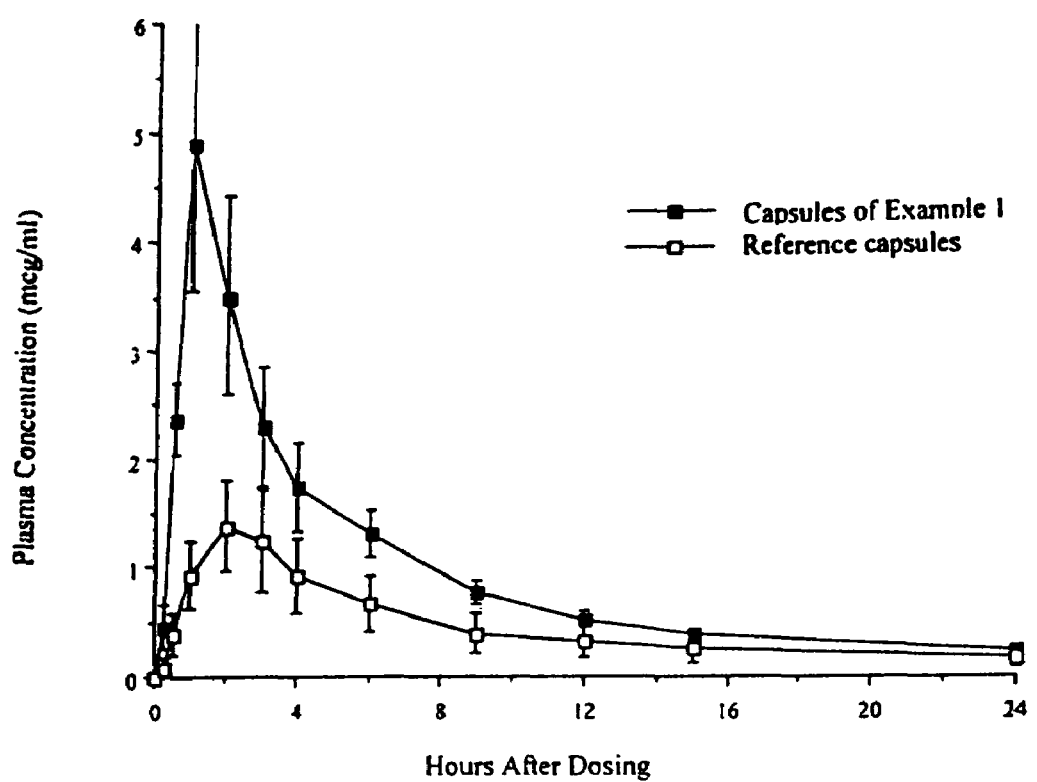
FIG. 1 is a graph showing the plasma concentration in fasted dogs of the formulation of Example 1 and a reference composition.

The bulk lipid-regulating agent can be prepared by any available method, as for example the compound fenofibrate may be prepared by the procedure disclosed in U.S. Pat. No. 4,058,552 or the procedure disclosed in U.S. Pat. No. 4,739,101, both herein incorporated by reference.

Representative structured lipids include, but are not limited to, caprylic/capric/lauric triglycerides, e.g., Captex 350™ (Abitec) and caprylic/capric/linoleic triglycerides, e.g., Captex 810 series (Abitec) and Miglyol 818 (Creanova), and in general, include those lipids containing saturated medium and long-chain fatty acids esterified to the same glycerol molecule. A preferred structured lipid is a caprylic/capric/lauric triglyceride, e.g., Captex 350™ (Abitec).

Suitable emulsifiers include pharmaceutically acceptable surfactants such as, for example, TPGS (d-alpha Tocopheryl Polyethylene Glycol 1000 Succinate), phospholipids, polyoxyethylene sorbitan fatty acid derivatives, castor oil or hydrogenated castor oil ethoxylates, polyglycerol esters of fatty acids, fatty acid ethoxylates, alcohol ethoxylates, polyoxyethylene-polyoxypropylene co-polymers and block co-polymers. Preferred emulsifiers include polyglycerol esters of fatty acids. A more preferred emulsifier is Caprol 6620, a polyglycerol-6 dioleate (Abitec).

Other optional ingredients which may be included in the compositions of the present invention are those which are conventionally used in oil-based drug delivery systems, e.g. antioxidants such as, for example, tocopherol, ascorbyl palmitate, ascorbic acid, butylated hydroxytoluene, butylated hydroxyanisole, propyl gallate, etc.; pH stabilizers such as, for example, citric acid, tartaric acid, fumaric acid, acetic acid, glycine, arginine, lysine, potassium hydrogen phosphate, etc.; thickeners/suspending agents such as, for example, hydrogenated vegetable oils, beeswax, colloidal silicon dioxide, gums, celluloses, silicates, bentonite, etc.; flavoring agents such as, for example, cherry, lemon, aniseed flavors, etc.; sweeteners such as aspartame, saccharin, cyclamates, etc.; and co-solvents such as, for example, ethanol, propylene glycol, dimethyl isosorbide, etc.

The solution comprising the lipid-regulating agent is prepared by dissolving said agent in the structured lipid with adequate mixing at or about room temperature. If an emulsifier is used, it is added to the structured lipid with mixing prior to addition of the lipid-regulating agent.

The resulting premix liquid comprising the lipid-regulating agent may be dosed directly for oral administration, diluted into an appropriate vehicle for oral administration, filled into soft or hard gelatin capsules for oral administration, or delivered by some other means obvious to those skilled in the art. The premix liquid can be used to improve the oral bioavailability, and/or increase the solubility of said agent.

The invention will be understood more clearly from the following non-limiting representative examples.

EXAMPLE 1

Miglyol 818 (Creanova) (8.3 gm) was added to a scintillation vial. Caprol 6G20 (polyglycerol-6 dioleate) (Abitec) (1.0 gm) was added to the vial and mixed until uniform. Fenofibrate (Sigma) (0.7 gm) was then added to the vial and mixed until it was completely dissolved. 957 mg. of the premix (containing 67 mg. fenofibrate) was added to each of six soft gelatin capsules using a syringe. The capsules were heat sealed and stored.

EXAMPLE 2

Miglyol 818 (Creanova)(9.3 gm) was added to a scintillation vial. Fenofibrate (Sigma) (0.7 gm) was added to the Miglyol and mixed until completely dissolved. 957 mg. of the premix (containing 67 mg. fenofibrate) was added to each of six soft gelatin capsules using a syringe. The capsules were heat sealed and stored.

EXAMPLE 3

Figure 2:
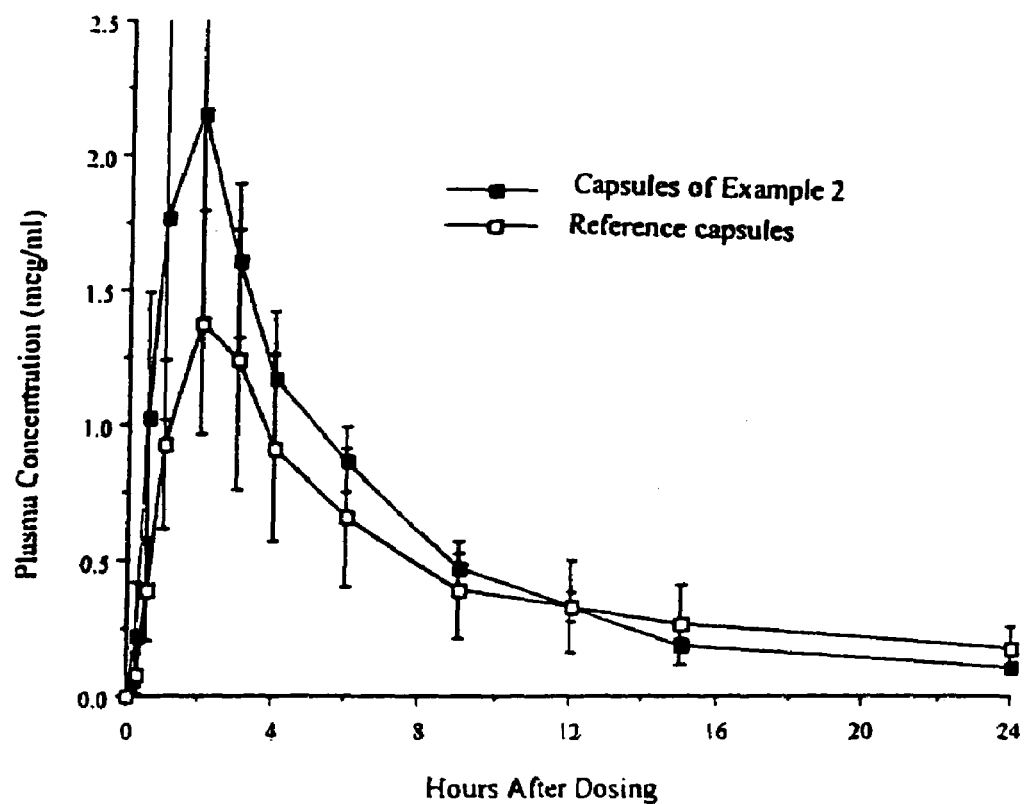
FIG. 2 is a graph showing the plasma concentration in fasted dogs of the formulation of Example 2 and a reference composition.

Capsules prepared by the process described in Example 1 and 2, and from a commercial fenofibrate composition, Lipanthyl 67M (Groupe Fournier) (Reference), were each administered to a group of fasted dogs at a dose of 67 mg/dog (one capsule per dog). The plasma concentrations of fenofibric acid were determined by HPLC. Concentrations were normalized to a 6.7 mg/kg dose in each dog. FIGS. 1 and 2 present the resulting data in graph form.

The results, provided as mean±SD, n=6 were as follows:

Lipanthyl 67M (Reference):
Cmax=1.88±0.97 mcg/ml
Tmax=1.6±0.9 hr
$t_{1/2}$=4.5 hr
AUC (0–24)=11.08±9.42 mcg·hr/ml
F(%)=21.1±11.8

Capsules of Example 1:
Cmax=5.13±3.12 mcg/ml
Tmax=1.0±0.5 hr
$t_{1/2}$=6.9 hr
AUC (0–24)=23.62±10.61 mcg·hr/ml
F(%)=49.1±21.9

The results, provided as mean±SD, n=6 were as follows:

Lipanthyl 67M (Reference):
Cmax=1.88±0.97 mcg/ml
Tmax=1.6±0.9 hr
$t_{1/2}$=4.5 hr
AUC (0–24)=11.08±9.42 mcg·hr/ml
F(%)=21.1±11.8

Capsules of Example 2:
Cmax=2.56±1.90 mcg/ml
Tmax=1.8±0.8 hr
$t_{1/2}$=5.4 hr
AUC (0–24)=13.47±6.62 mcg·hr/ml
F(%)=27.9±13.6

The invention claimed is:

1. A composition consisting of a fibrate dissolved in at least one structured lipid.

2. A composition of claim 1 wherein the fibrate is fenofibrate.

3. A composition of claim 1 wherein at least one or more of the structured lipids is selected from the group consisting of caprylic/capric/lauric triglycerides and caprylic/capric/linoleic triglycerides.

4. A composition of claim 3 wherein the structured lipid is a caprylic/capric/lauric triglyceride.

5. A capsule comprising a composition of claim 1.

6. A capsule of claim 5 wherein the fibrate is fenofibrate.

7. A method of treating hyperlipidemia comprising the step of administering a therapeutically-effective amount of a composition of claim 1 to a patient.

8. A method of treating hyperlipidemia comprising the step of administering a therapeutically-effective amount of a composition of claim 2 to a patient.

* * * * *